US010632061B2

(12) United States Patent
Constantine et al.

(10) Patent No.: US 10,632,061 B2
(45) Date of Patent: Apr. 28, 2020

(54) SUNSCREEN COMPOSITION IN POWDER FORM

(71) Applicant: COSMETIC WARRIORS LIMITED, Poole, Dorset (GB)

(72) Inventors: Mark Constantine, Poole (GB); Margaret Joan Constantine, Poole (GB); Helen Elizabeth Ambrosen, Wimborne (GB); Rowena Jacqueline Bird, Christchurch (GB); Daniel Campbell, Poole (GB)

(73) Assignee: COSMETIC WARRIORS LIMITED, Poole, Dorset (GB)

( * ) Notice: Subject to any disclaimer, the term of this patent is extended or adjusted under 35 U.S.C. 154(b) by 0 days.

(21) Appl. No.: 15/319,187

(22) PCT Filed: Jun. 10, 2015

(86) PCT No.: PCT/GB2015/051708
§ 371 (c)(1),
(2) Date: Dec. 15, 2016

(87) PCT Pub. No.: WO2015/193644
PCT Pub. Date: Dec. 23, 2015

(65) Prior Publication Data
US 2017/0151168 A1 Jun. 1, 2017

(30) Foreign Application Priority Data
Jun. 19, 2014 (GB) .................................. 1410905.2

(51) Int. Cl.
| A61K 8/92 | (2006.01) |
| A61K 8/27 | (2006.01) |
| A61K 8/29 | (2006.01) |
| A61Q 17/04 | (2006.01) |
| A61K 8/02 | (2006.01) |
| A61K 8/26 | (2006.01) |
| A61K 8/19 | (2006.01) |
| A61K 8/35 | (2006.01) |
| A61K 8/37 | (2006.01) |
| A61K 8/40 | (2006.01) |
| A61K 8/96 | (2006.01) |

(52) U.S. Cl.
CPC .............. *A61K 8/922* (2013.01); *A61K 8/022* (2013.01); *A61K 8/0216* (2013.01); *A61K 8/19* (2013.01); *A61K 8/26* (2013.01); *A61K 8/27* (2013.01); *A61K 8/29* (2013.01); *A61K 8/35* (2013.01); *A61K 8/37* (2013.01); *A61K 8/40* (2013.01); *A61K 8/965* (2013.01); *A61Q 17/04* (2013.01); *A61K 2800/30* (2013.01); *A61K 2800/31* (2013.01); *A61K 2800/43* (2013.01)

(58) Field of Classification Search
None
See application file for complete search history.

(56) References Cited

U.S. PATENT DOCUMENTS

| 5,904,918 A | 5/1999 | Sterphone et al. |
| 2001/0055573 A1 | 12/2001 | Debiasi et al. |
| 2003/0082119 A1 | 5/2003 | Golz-Berner et al. |
| 2005/0187128 A1 | 8/2005 | Martin et al. |
| 2006/0078514 A1* | 4/2006 | Bertz ..................... A61K 8/37 424/59 |
| 2011/0318286 A1 | 12/2011 | Kawasaki et al. |
| 2014/0294975 A1* | 10/2014 | Fageon ................ A61K 8/0225 424/489 |

FOREIGN PATENT DOCUMENTS

| EP | 0418443 A1 | 3/1991 |
| EP | 1530964 A1 | 5/2005 |
| FR | 2982148 A1 * | 5/2013 ........... A61K 8/0225 |
| FR | 2982148 A1 | 5/2013 |
| JP | H03-112921 A | 5/1991 |
| JP | H06-009359 A | 1/1994 |
| JP | 2005-170860 A | 6/2005 |
| JP | 2005-1456972 A | 6/2005 |
| JP | 2013-075868 A | 4/2013 |
| JP | 2013-512233 A | 4/2013 |
| JP | 2014-532676 A | 12/2014 |
| RU | 2359657 C2 | 6/2009 |
| WO | 2007/078062 A1 | 7/2007 |
| WO | 2011/064555 A2 | 6/2011 |

(Continued)

OTHER PUBLICATIONS

Food and Drug Administration, 21 CFR Parts 310, 352, 700, and 740 as published in Federal Register/vol. 64, No. 98 (1999)/Rules and Regulations, pp. 27666-27693.

(Continued)

*Primary Examiner* — Carlos A Azpuru
*Assistant Examiner* — Casey S Hagopian
(74) *Attorney, Agent, or Firm* — Merchant & Gould P.C.

(57) ABSTRACT

A sunscreen in powder form includes vegetable oil, vegetable butter, wax or mixture thereof. Vegetable oil, vegetable butter and wax are present in a total amount of from 1 to 25% by weight of the sunscreen. One or more UV absorbing materials are present in an amount of from 10 to 40% by weight of the sunscreen. One or more UV reflecting materials are present in an amount of from 30 to 85% by weight of the sunscreen. One or more anti-caking agents are present in an amount of from 5 to 25% by weight of the sunscreen.

31 Claims, No Drawings

(56) References Cited

FOREIGN PATENT DOCUMENTS

WO  2012/175970 A2  12/2012
WO  2013/068236 A1  5/2013

OTHER PUBLICATIONS

International Search Report and Written Opinion for PCT/GB2015/051708, dated Aug. 18, 2015.
Office Action for Russian Patent Application No. 2017101426, dated Nov. 7, 2018.
H. Mineo et al., "Study on Bridge Formation Mechanism between NaCl Crystals and Functions of Anti-caking Agents" Bulletin of the Society of Sea Water Science, Japan, 63(3): 183-189 (2009).
Office Action for Japanese Patent Application No. 2016-571226, dated Feb. 5, 2019.
Office Action for Japanese Patent Application No. 2016-571226, dated Sep. 10, 2019.

* cited by examiner

SUNSCREEN COMPOSITION IN POWDER FORM

This application is a National Stage of PCT/GB2015/051708, filed 10 Jun. 2015, which claims benefit of 1410905.2, filed 19 Jun. 2014 in Great Britain which applications are incorporated herein by reference. To the extent appropriate, a claim of priority is made to each of the above disclosed applications.

FIELD OF THE INVENTION

The present invention relates to a sunscreen, a process for producing said sunscreen, and a product prepared by the method.

BACKGROUND TO THE INVENTION

The present invention relates to products particularly those for use in contact with the human body.

Sunscreens are any type of topical product that can absorb or reflect Ultraviolet A (UVA) or Ultraviolet B (UVB) radiation from sunlight, and therefore help protect the skin against sunburn and other potential harmful effect of the sun. Excessive UV radiation exposure is the leading cause of primarily non-malignant skin tumours.

The first sunscreen was reported to have been invented by Franz Greiter in 1938; the product 'Glacier Cream' became the basis for Piz Buin company, who took their name from the area in Switzerland that inspired Greiter's cream. Greiter in 1962 also developed the concept of a Sun Protection Factor, which has become the worldwide standard for measuring the efficacy of sunscreens when applied at an even rate of 2 milligrams per square centimetre ($mg/cm^2$).

The Ultraviolet radiation has different properties dependant on its wavelength. The UV spectra can be split into 3 types, as discussed below:
1. UVA radiation penetrates the skin more deeply than UVB or UVC (which is blocked by the Ozone layer) reaching the dermis through the epidermis. The effect of UVA exposure on the skin includes pigment darkening, photo aging and indirect DNA damage which can lead to the formation of cancerous cells.

Protection from UVA radiation is measured using 2 standard tests—Persistent Pigment Darkening and an In-Vitro UVA test. In Japan products receive either a PA+, PA++ or PA+++ rating depending on their efficacy. In Europe, the COLIPA UVA symbol can be applied to products whose UVA Protection Factor is at least ⅓ of the SPF value.
2. UVB mostly penetrates the skin only as far as the epidermis and exposure only occurs outdoors. The effect of UVB radiation includes sunburn, delayed tan, skin thickening and direct DNA damage. UVB protection is investigated using the Sun Protection Factor test. The SPF is derived from the smallest dose causing an erythema (reddening of the skin) with sunscreen compared to without sunscreen.
3. UVC, which doesn't reach the earth, as it is blocked by the ozone layer.

There are two types of sunscreen agents, UV reflectors (Physical Sunscreens) and UV absorbers (Chemical Sunscreens).
1. UV reflectors or physical sunscreens protect the skin from the sun by deflecting or blocking the sun's rays. Titanium Dioxide and Zinc Oxide are the most commonly used physical sunscreens, as they are inorganic particles they cannot be absorbed by the body. Therefore they can form a filter on the skin which reflects or scatters UV radiation. Zinc Oxide is the only true UV reflector as Titanium Dioxide has both reflector and absorber properties. Zinc oxide is particularly good at reflecting UVA radiation. UV reflectors by nature tend to be thicker than UV reflectors and are often harder to apply. They also tend to leave the skin white or tinted. In addition, as they are a physical medium they tend to rub off more easily and therefore have to be reapplied more frequently.
2. UV absorbers or Chemical Sunscreens absorb the UVA and UVB radiation and convert them into harmless heat. An important feature is that the absorber molecules convert the energy without reacting with other molecules or being destroyed. These filters respond to the UV radiation by undergoing a short-term internal rearrangement reaction known as a H shift. The absorbed UV radiation stimulates the molecule and one hydrogen atom migrates to a different position inside the molecule. When converted back into its original state, the energy absorbed as UV light is gradually released as heat, allowing the molecule to absorb further radiation. This mechanism ensures effective and long-lasting protection. They tend to be colourless, odourless and runny which makes them the ideal ingredients for sunscreen creams or lotions.

Physical sunscreens (UV reflectors) tend to be better tolerated by most skin types and are particularly goo for sensitive skin. However, they tend to leave a white cast or white streaks after application and don't offer as much UVA protection compared to chemical sunscreens. Physical sunscreens present in lotions are also a bit thicker so they are often more difficult to apply. Physical sunscreens are difficult to formulate with, thus require thicker and heavier bases or emulsions to ensure stability. Since reflectors and absorbers have their advantages and disadvantages, many of today's sunscreens contain both UV filters. However, knowing whether a sunscreen is physical, chemical, or both does not give enough information about whether a particular sunscreen will be a protective one. The most effective sunscreens provide protect across the entire UVA/UVB spectrum.

The general public have a perfunctory attitude to cosmetic lotions that provide protection from UVA and UVB radiation from sunlight. Consumers only apply sunscreen lotions when the weather conditions obviously demand it and the lotions within this field offer limited functionality when it comes to the considering the various requirements from the general public. This can often lead to the consumer either using the incorrect product, in the incorrect manner or potentially not protecting themselves at all from the harmful effects of the sun.

The present invention seeks to provide a sunscreen that addresses the problems of the prior art.

SUMMARY OF THE INVENTION

The present invention relates to a sunscreen that can be readily applied by the user. The sunscreen is in the form of a powder product which can be applied to skin, leaving the skin protected from UV radiation.

In a first aspect, there is provided a sunscreen in powder form comprising (i) vegetable oil, vegetable butter, wax or mixture thereof, wherein vegetable oil, vegetable butter and wax are present in a total amount of from 1 to 25% by weight of the sunscreen, (ii) one or more UV absorbing materials, wherein UV absorbing material is present in an amount of from 10 to 40% by weight of the sunscreen, and (iii) one or more UV reflecting materials, wherein UV reflecting material is present in an amount of from 30 to 85% by weight of the sunscreen, (iv) one or more anti-caking agents, wherein anti-caking agent is present in an amount of from 5 to 25% by weight of the sunscreen.

In a second aspect, there is provided a process for the production of a sunscreen in solid form comprising (i) vegetable oil, vegetable butter, wax or mixture thereof, wherein vegetable oil, vegetable butter and wax are present in a total amount of from 1 to 25% by weight of the sunscreen, (ii) one or more UV absorbing materials, wherein UV absorbing material is present in an amount of from 10 to 40% by weight of the sunscreen, and (iii) one or more UV reflecting materials, wherein UV reflecting material is present in an amount of from 30 to 85% by weight of the sunscreen, (iv) one or more anti-caking agents, wherein anti-caking agent is present in an amount of from 5 to 25% by weight of the sunscreen.
the process comprising the steps of
(a) when the vegetable oil, vegetable butter, wax or mixture thereof is solid, heating the vegetable oil, vegetable butter, wax or mixture thereof to provide a liquid
(b) mixing the one or more UV absorbing materials, and the one or more UV reflecting materials, with the liquid vegetable oil, vegetable butter, wax or mixture thereof
(c) cooling the mixture to provide the sunscreen powder.

In a third aspect, there is provided use of a sunscreen for reducing the damage to skin of a user by sunlight, wherein the sunscreen is in powder form and comprises
(i) vegetable oil, vegetable butter, wax or mixture thereof, wherein vegetable oil, vegetable butter and wax are present in a total amount of from 1 to 25% by weight of the sunscreen,
(ii) one or more UV absorbing materials, wherein UV absorbing material is present in an amount of from 10 to 40% by weight of the sunscreen, and
(iii) one or more UV reflecting materials, wherein UV reflecting material is present in an amount of from 30 to 85% by weight of the sunscreen,
(iv) one or more anti-caking agents, wherein anti-caking agent is present in an amount of from 5 to 25% by weight of the sunscreen.

In a fourth aspect, there is provided a method of applying a sunscreen comprising the step(s) of applying to the skin of a user a sunscreen in powder form comprising
(i) vegetable oil, vegetable butter, wax or mixture thereof, wherein vegetable oil, vegetable butter and wax are present in a total amount of from 1 to 25% by weight of the sunscreen,
(ii) one or more UV absorbing materials, wherein UV absorbing material is present in an amount of from 10 to 40% by weight of the sunscreen, and
(iii) one or more UV reflecting materials, wherein UV reflecting material is present in an amount of from 30 to 85% by weight of the sunscreen,
(iv) one or more anti-caking agents, wherein anti-caking agent is present in an amount of from 5 to 25% by weight of the sunscreen.

The nature of the sunscreen powder is such that it may be applied liberally to the body. By the liberal application of the powder it is meant to be applied in a similar manner as a sunscreen lotion, whilst providing the benefits of a dry powder, which leaves the skin feeling softened and mattified. This addresses the problems of the lotions of the prior art, which leave an oily residue or sticky feeling which discourages users from applying the product. Once the user is dressed, the application of a sunscreen lotion risks contacting the user's clothes resulting in staining etc. The dry powder will not stain clothing or other materials and can be easily brushed away. Thus the present invention provides a sunscreen which is more likely to be applied by the user.

For ease of reference, these and further aspects of the present invention are now discussed under appropriate section headings. However, the teachings under each section are not necessarily limited to each particular section.

DETAILED DESCRIPTION

Composition

As discussed herein, in one aspect of the present invention, there is provided a sunscreen in powder form comprising (i) vegetable oil, vegetable butter, wax or mixture thereof, wherein vegetable oil, vegetable butter and wax are present in a total amount of from 1 to 25% by weight of the sunscreen, (ii) one or more UV absorbing materials, wherein UV absorbing material is present in an amount of from 10 to 40% by weight of the sunscreen, and (iii) one or more UV reflecting materials, wherein UV reflecting material is present in an amount of from 30 to 85% by weight of the sunscreen, (iv) one or more anti-caking agents, wherein anti-caking agent is present in an amount of from 5 to 25% by weight of the sunscreen.

As discussed herein, the sunscreen is a powder. Powdered products of the present invention are compositions which are in the form of fine free-flowing particles. Such powders may be dispensed from a container in a similar fashion to a lotion. Thus, they possess the benefits of a lotion e.g. ease of application/convenience, with the benefits of a dry powder, which has the effect of leaving the skin softened and mattified.

The sunscreen powder of the present invention may have a melting point above 200° C. This offers further advantages because at high temperatures other solid sunscreens often melt and lotions separate.

Vegetable Oil, Vegetable Butter, Wax or Mixtures Thereof

The sunscreen of the present invention contains vegetable oil, vegetable butter, wax or mixture thereof in a total amount of from 1 to 25% by weight of the sunscreen, Preferably the sunscreen comprises vegetable oil, vegetable butter, wax or mixture thereof in a total amount of from 1 to 20% by weight of the sunscreen, such as in a total amount of from 1 to 17% by weight of the sunscreen, such as in a total amount of from 1 to 15% by weight of the sunscreen, such as in a total amount of from 1 to 12% by weight of the sunscreen, such as in a total amount of from 1 to 10% by weight of the sunscreen, such as in a total amount of from 1 to 8% by weight of the sunscreen, such as in a total amount of from 1 to 6% by weight of the sunscreen, such as in a total amount of from 2 to 6% by weight of the sunscreen, such as in a total amount of from 3 to 5% by weight of the sunscreen, such as in a total amount of approximately 4% by weight of the sunscreen.

The vegetable oil, vegetable butter and wax may be selected from any materials suitable to achieve the purpose of the present invention. In one preferred aspect, the vegetable oil, vegetable butter and wax are selected from cocoa butter, murumuru butter, cupuacu butter, illipe butter, mango butter, sesame oil, rosehip oil, almond oil, raspberry seed oil, beeswax, rapeseed wax, japan wax and mixtures thereof.

UV Absorbing Material

The sunscreen of the present invention contains a UV absorbing material. As discussed herein, UV absorbers absorb the UVA and/or UVB radiation and convert them into harmless heat. An important feature is that the absorber molecules convert the energy without reacting with other molecules or being destroyed. These filters respond to the UV energy by undergoing a short-term internal rearrangement. When converted back into its original state, the energy absorbed as UV light is gradually released as heat, allowing the molecule to absorb further radiation.

The UV absorbing material of the present invention is a material that absorbs at least UVA or UVB radiation. In one aspect, the UV absorbing material absorbs both UVA and UVB radiation. It will be appreciated by one skilled in the art that the present invention encompasses aspects where the sunscreen composition contains one material which absorbs UVA radiation and another material which absorbs UVB radiation. By UV absorbing, it is meant a material that absorbs radiation in the ultraviolet range at wavelengths of 290 to 400 nanometres.

Preferably the sunscreen comprises UV absorbing material in an amount of from 10 to 35% by weight of the sunscreen, such as in an amount of from 10 to 30% by weight of the sunscreen, such as in an amount of from 10 to 25% by weight of the sunscreen, such as in an amount of from 15 to 30% by weight of the sunscreen, such as in an amount of from 15 to 25% by weight of the sunscreen, such as in an amount of from 17 to 23% by weight of the sunscreen, such as in an amount of from 18 to 22% by weight of the sunscreen, such as in an amount of approximately 20% by weight of the sunscreen.

The UV absorbing material may be selected from any materials suitable to achieve the purpose of the present invention. In one preferred aspect, the UV absorbing material is selected from octocrylene, octyl methoxycinnamate, butylmethoxydibenzoylmethane, homosalate, ecamsule, and mixtures thereof.

UV Reflecting Material

The sunscreen of the present invention contains a UV reflecting material. As discussed herein, UV reflecting materials protect the skin from the sun by deflecting or blocking the sun's rays.

One benefit of sunscreen powders is that the composition of UV reflecting materials in sunscreens can be higher in powders than in lotions. This is due to the fact that lotions with high UV reflecting materials compositions will separate readily, whilst powders can maintain a uniform composition containing a higher proportion of UV reflecting materials.

The UV reflecting material of the present invention reflects at least UVA or UVB radiation. In one aspect, the UV reflecting material reflects both UVA and UVB radiation. It will be appreciated by one skilled in the art that the present invention encompasses aspects where the sunscreen composition contains one material which reflects UVA radiation and another material which reflects UVB radiation. By UV reflecting, it is meant a material that reflects or scatters radiation in the ultraviolet range at wavelengths of 290 to 400 nanometres.

Preferably the sunscreen comprises UV reflecting material in an amount of from 30 to 80% by weight of the sunscreen, such as in an amount of from 30 to 75% by weight of the sunscreen, such as in an amount of from 30 to 65% by weight of the sunscreen, such as in an amount of from 30 to 60% by weight of the sunscreen, such as in an amount of from 30 to 55% by weight of the sunscreen, such as in an amount of from 35 to 55% by weight of the sunscreen, such as in an amount of from 30 to 50% by weight of the sunscreen, such as in an amount of from 35 to 50% by weight of the sunscreen, such as in an amount of from 35 to 45% by weight of the sunscreen, such as in an amount of from 40 to 45% by weight of the sunscreen, such as in an amount of approximately 42% by weight of the sunscreen.

The UV reflecting material may be selected from any materials suitable to achieve the purpose of the present invention. In one preferred aspect, the UV reflecting material is selected from clays, zinc oxide, titanium dioxide and mixtures thereof.

One preferred aspect, the UV reflecting material comprises at least a clay. In this aspect, the claim may be used alone or in combination with other materials. For example, the UV reflecting material may comprise at least (i) a clay and (ii) at least one of zinc oxide and titanium dioxide.

The clay may be selected from suitable known clays, which may act as UV reflective materials. In one aspect, the clay is selected from calamine, kaolin, talc, rhassoul mud powder, mica and mixtures thereof.

It will be appreciated by one skilled in the art that the nature of UV reflecting materials are such that they may reflect other wavelengths of the visible spectrum. In this respect, the UV reflecting material may also act as a pigment. The sunscreen may contain pigments in addition to the essential components recited herein. If the pigment is a UV reflecting material then the amount of pigment is to be incorporated in the total of UV reflecting material defined herein. Thus in one aspect the sunscreen may further comprise a pigment. The pigment may or may not be a UV reflecting material.

UV Absorbing and UV Reflecting Materials

It will be appreciated by one skilled in the art that the UV absorbing and UV reflecting materials may have to be selected from materials which have undergone regulatory approval. In one aspect the UV absorbing and UV reflecting materials are selected from materials approved in Food and Drug Administration, 21 CFR Parts 310, 352, 700, and 740. In one aspect the UV absorbing and UV reflecting materials are selected from materials approved in Food and Drug Administration, 21 CFR Parts 310, 352, 700, and 740 as published in Federal Register/Vol. 64, No. 98/Friday, May 21, 1999/Rules and Regulations.

In one aspect the UV absorbing and UV reflecting materials are selected from a group consisting of aminobenzoic acid (PABA), avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, titanium dioxide, trolamine salicylate, zinc oxide and mixtures thereof.

Anti-Caking Agent

The sunscreen of the present invention contains an anti-caking agent. The nature of anti-caking agents is known in the art. These materials An prevent or inhibit the formation of lumps and thereby ease production, packaging, transport, and/or consumption. As discussed herein, the anti-caking component prevents the powder from clumping together to form a solid, enabling a free-flowing powder form of sunscreen.

In one aspect the anti-caking agent is selected from the group consisting of calcium carbonate, magnesium carbonate, tricalcium phosphate, powdered cellulose, magnesium stearate, sodium bicarbonate, sodium ferrocyanide, potassium ferrocyanide, calcium ferrocyanide, bone phosphate, sodium silicate, silicon dioxide, calcium silicate, magnesium trisilicate, talcum powder, sodium aluminosilicate, potassium aluminium silicate, calcium aluminosilicate, bentonite, aluminium silicate, stearic acid, polydimethylsiloxane and mixtures thereof.

In one aspect the anti-caking agent is selected from the group consisting of calcium carbonate, magnesium carbonate and mixtures thereof.

In one aspect the anti-caking agent is at least magnesium carbonate. In one aspect the anti-caking agent is magnesium carbonate. Thus in a further aspect the present invention provides a sunscreen in powder form comprising (i) vegetable oil, vegetable butter, wax or mixture thereof, wherein vegetable oil, vegetable butter and wax are present in a total amount of from 1 to 25% by weight of the sunscreen, (ii) one or more UV absorbing materials, wherein UV absorbing material is present in an amount of from 10 to 40% by weight of the sunscreen, and (iii) one or more UV reflecting materials, wherein UV reflecting material is present in an amount of from 30 to 85% by weight of the sunscreen, (iv) magnesium carbonate, wherein the magnesium carbonate is present in an amount of from 5 to 25% by weight of the sunscreen.

It will be appreciated by one skilled in the art that the characteristics of magnesium carbonate make it a commonly used ingredient in cosmetic powders. Magnesium carbonate is able to absorb water and oils in addition to acting as a moisture stabiliser, which helps the powder stick to the surface of the skin upon application. The rheological properties of magnesium carbonate give the powdered sunscreen the ability to flow on to the skin in a similar fashion to a lotion.

The magnesium carbonate has the added characteristic of mattifying the skin on application of the sunscreen. It reduces the oily sensation of the butters, oils and waxes to create a feeling of softened, dry skin.

Preferably the sunscreen comprises anti-caking agents such as magnesium carbonate in an amount of from 10 to 25% by weight of the sunscreen, such as in an amount of from 5 to 20% by weight of the sunscreen, such as in an amount of from 5 to 15% by weight of the sunscreen, such as in an amount of from 7 to 15% by weight of the sunscreen, such as in an amount of from 10 to 15% by weight of the sunscreen, such as in an amount of approximately 12% by weight of the sunscreen.

Starches

The sunscreen of the present invention may contain starches. Starches absorb moisture and condition skin.

It will be appreciated by one skilled in the art that the characteristics of starches enable them to be used in cosmetic powders. Starches are able to absorb water and oils, which help the powder stick to the surface of the skin upon application, in addition to imparting fragrances. Starches are high in skin conditioning agents, such as vitamins and essential minerals, which reduce swelling, softens skin and maintains skin's health. The overall benefit provides for a sunscreen which is easy to apply, provides a fresh dry feeling to the skin and maintains the skins health.

The starches may be selected from suitable known starches. In one aspect, the starch is selected from corn starch, potato flour and mixtures thereof.

Further Components

The sunscreen may contain one or more additional components such as to provide the desired composition. In one aspect the sunscreen powder further comprising at least one additional component selected from humectants, surfactants, fruits, vegetables, herbs, seaweeds, cereals, beans, proteins, binders, fillers, dispersants, opacifiers, perfumes, colours, fragrances and mixtures thereof. In one aspect, the sunscreen comprising a further component selected from binders, fillers, fruits, vegetables, humectants, dispersants and mixtures thereof.

In one aspect the sunscreen contains one or more fragrances. Preferably the sunscreen comprises fragrance in an amount of no greater than 5% by weight of the sunscreen. If present, fragrance may be present in an amount of from 0.1 to 5% by weight of the total composition. The amount of fragrance is preferably from 0.1% to 5% by weight of the total composition, such as from 0.1% to 4% by weight of the total composition, such as from 0.5% to 5% by weight of the total composition, such as from 1% to 5% by weight of the total composition, such as from 0.5% to 4% by weight of the total composition, such as from 0.5% to 3% by weight of the total composition, such as from 0.5% to 2.5% by weight of the total composition, such as from 1.5% to 2.5% by weight of the total composition. Alternatively, in one aspect, the sunscreen is fragrance free.

The essential oils may be selected based on the fragrance desired, skin type to be treated and other effects desired based on the well-known properties of essential oils. The addition of essential oils, when taken in to the nose, is known to alter mood. For example, essential oils are known to create effects of drowsiness or stimulating the senses. Many effects can be achieved by the use of essential oils.

In one embodiment, the one or more essential oils present in the product are selected from Rosewood, Sandalwood, Chamomile, *Eucalyptus*, Tonka absolute, Lemon myrtle, Jasmin, Ylang ylang, Labdanum, Lemongrass, Rose Absolute, Grapefruit, Patchouli, Rosemary, Armois, Lemon, Neroli, Sweet violet, Lavender, Orange 50 fold, Vanilla, Peppermint, Benzoin, Hydrangia, *Litsea Cubeba*, Cardamon, Tonka, and Chamomile blue. In one embodiment, the one or more essential oils present in the product are selected from Rosewood, Sandalwood, Chamomile, *Eucalyptus*, Lavender, Tonka absolute, Rose absolute.

Vitamins, particularly B, C and E are very beneficial for the skin. Vitamin rich ingredients such as Wheatgerm oil can also be used to deliver vitamins on to the skin. In a one embodiment, the vitamins are selected from vitamin B, vitamin C, vitamin E and mixtures thereof. It will be appreciated by one skilled in the art that the vitamin may be provided from any suitable source. For example the vitamin(s) may be provided from a synthetic source or from incorporation into the product of a material, such as a natural material, that has a high vitamin content.

In one aspect the sunscreen further comprises a colorant material. If present, colorant materials may be present in an amount of from 0.001 to 3% by weight of the total composition.

In one aspect the sunscreen contains a humectant. In one aspect, the humectant is selected from honey, glycerine, sorbitol, agave nectar, fruit syrups, herbal syrups and mixtures thereof. Preferably the humectant is selected from honey, glycerine, sorbitol and mixtures thereof.

In one aspect the sunscreen further comprises a filler. The filler may be talc.

In one aspect the solid sunscreen contains a dispersant. The dispersant is present to assist with the dispersion of the UV reflecting agent, such as a clay, in the oils, fats, waxes or mixtures thereof. In one aspect, the dispersant may be magnesium carbonate.

In one aspect the sunscreen contains water. In one aspect the sunscreen is free or substantially free of water. Preferably the sunscreen comprises water in an amount of no greater than 5% by weight of the sunscreen, such as in an amount of no greater than 4% by weight of the sunscreen, such as in an amount of no greater than 3% by weight of the sunscreen, such as in an amount of no greater than 2% by weight of the sunscreen, such as in an amount of no greater than 1% by weight of the sunscreen, such as in an amount of no greater than 0.5% by weight of the sunscreen, such as in an amount of no greater than 0.1% by weight of the sunscreen, such as in an amount of no greater than 0.01% by weight of the sunscreen.

In one aspect the sunscreen contains preservatives. In one aspect the sunscreen is free or substantially free of preservatives. Preferably the sunscreen comprises preservatives in an amount of no greater than 5% by weight of the sunscreen, such as in an amount of no greater than 4% by weight of the sunscreen, such as in an amount of no greater than 3% by weight of the sunscreen, such as in an amount of no greater than 2% by weight of the sunscreen, such as in an amount of no greater than 1% by weight of the sunscreen, such as in an amount of no greater than 0.5% by weight of the sunscreen, such as in an amount of no greater than 0.1% by weight of the sunscreen, such as in an amount of no greater than 0.01% by weight of the sunscreen.

Method

As discussed herein, in one aspect the present invention provides a method of applying a sunscreen comprising the step(s) of applying to the skin of a user a sunscreen in powder form comprising
  (i) vegetable oil, vegetable butter, wax or mixture thereof, wherein vegetable oil, vegetable butter and wax are present in a total amount of from 1 to 25% by weight of the sunscreen,
  (ii) one or more UV absorbing materials, wherein UV absorbing material is present in an amount of from 10 to 40% by weight of the sunscreen, and
  (iii) one or more UV reflecting materials, wherein UV reflecting material is present in an amount of from 30 to 85% by weight of the sunscreen,
  (iv) one or more anti-caking agents, wherein anti-caking agent is present in an amount of from 5 to 25% by weight of the sunscreen.

The method of applying the sunscreen is typically performed by the user applying the sunscreen to dry skin. In a preferred aspect the sunscreen is applied to dry skin, such as applied as a stand-alone sunscreen, such as applied as an additive to other cosmetic products, such as applied as a supplement to other cosmetic products containing UV absorbing and UV reflecting components.

In one aspect the sunscreen is a supplement, wherein the sunscreen is added to a product with an existing SPF rating to increase the overall SPF value.

In one aspect the sunscreen is an additive, wherein the sunscreen is added to a product with no SPF value to provide protection from UV radiation in addition to the base product, such as a moisturiser or foundation.

The invention will now be described with reference to the following non-limiting example.

Example—Powder Sunscreen

The following composition was prepared in accordance with the method below.

| Phase | Formula % | Raw Material Type | Batch Size: g |
|---|---|---|---|
| A | 2.0 | Mango Butter | 20.000 |
|   | 0.2 | Rapeseed Wax | 2.000 |
|   | 1.8 | Rosehip Oil | 18.000 |
|   | 8.0 | Homosalate | 80.000 |
|   | 8.0 | Octocrylene | 80.000 |
|   | 4.0 | Butylmethoxydibenzoylmethane | 40.000 |
|   |   |   | 0.000 |
| B | 10.0 | Kaolin | 100.000 |
|   | 32.0 | Calamine Powder (zinc oxide) | 320.000 |

| Phase | Formula % | Raw Material Type | Batch Size: g |
|---|---|---|---|
| C | 12.0 | Magnesium Carbonate | 120.000 |
|   | 20.0 | Potato Flour | 200.000 |
|   |   |   | 0.000 |
|   | 2.0 | Fragrance | 20.000 |
|   | 100.000 |   | 1000.000 |

1. Phase A containing the vegetable oils, vegetable butters and waxes, as well as the oil soluble sunscreens, were heated together to between 50° C.-60° C. to form a liquid.
2. Phase B containing all the components in powdered form were then sieved and ground together to create a powder with a uniform particle size.
3. The oil phase and powder phase were blended together in a controlled manner to prevent clumping within the powder.
4. The controlled blending of the two phases cooled the mixture slowly after which the powder was sieved and ground for a second time to ensure equal distribution and absorption of all liquid phase components, most importantly the oil soluble sunscreens, and a powder with a uniform particle size was achieved.

This process ensures a consistently high quality UV protective product.

The sunscreen was tested for its UV protective rating. The sunscreen was tested to determine its Sun Protection Factor (SPF), UVA Protection Factor (UVA-PF) and PA rating. The powder sunscreen products achieved
  an SPF value of 15;
  a UVA-PF value of 5.5 and
  a PA++ rating.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

The invention claimed is:
1. A sunscreen in powder form comprising:
  (i) at least one vegetable butter and optionally, vegetable oil, wax, or a mixture of vegetable butter, vegetable oil and/or wax, wherein the vegetable oil, vegetable butter and wax are present in a total amount of from 1 to 25% by weight of the sunscreen,
  (ii) one or more UV absorbing materials, wherein UV absorbing material is present in an amount of from 10 to 40% by weight of the sunscreen,
  (iii) one or more UV reflecting materials, wherein UV reflecting material is present in an amount of from 30 to 85% by weight of the sunscreen,
  (iv) one or more anti-caking agents, wherein anti-caking agent is present in an amount of from 5 to 25% by weight of the sunscreen, and
  (v) one or more starches.
2. The sunscreen according to claim 1, wherein the sunscreen is an additive.
3. The sunscreen according to claim 1, wherein the sunscreen is a supplement.

4. The sunscreen according to claim 1, wherein the sunscreen comprises vegetable oil, vegetable butter, wax or mixture thereof in a total amount of from 1 to 20% by weight of the sunscreen.

5. The sunscreen according to claim 1, wherein the sunscreen comprises vegetable oil, vegetable butter, wax or mixture thereof in a total amount of from 1 to 17% by weight of the sunscreen.

6. The sunscreen according to claim 1, wherein the vegetable oil, vegetable butter and wax are selected from cocoa butter, murumuru butter, cupuacu butter, illipe butter, mango butter, sesame oil, rosehip oil, almond oil, raspberry seed oil, beeswax, rapeseed wax, Japan wax and mixtures thereof.

7. The sunscreen according to claim 1, wherein the sunscreen comprises UV absorbing material in an amount of from 10 to 30% by weight of the sunscreen.

8. The sunscreen according to claim 1, wherein the sunscreen comprises UV absorbing material in an amount of from 15 to 25% by weight of the sunscreen.

9. The sunscreen according to claim 1, wherein the UV absorbing material is selected from octocrylene, octyl methoxycinnamate, butylmethoxydibenzoylmethane, homosalate, ecamsule, and mixtures thereof.

10. The sunscreen according to claim 1, wherein the sunscreen comprises UV reflecting material in a total amount of from 30 to 70% by weight of the sunscreen.

11. The sunscreen according to claim 1, wherein the sunscreen comprises UV reflecting material in a total amount of from 30 to 50% by weight of the sunscreen.

12. The sunscreen according to claim 1, wherein the UV reflecting material is selected from clays, zinc oxide, titanium dioxide and mixtures thereof.

13. The sunscreen according to claim 1, wherein the UV reflecting material comprises at least zinc oxide.

14. The sunscreen according to claim 1, wherein the UV reflecting material comprises at least (i) at least one of zinc oxide and titanium dioxide and (ii) a clay.

15. The sunscreen according to claim 1, wherein the clay is selected from kaolin, talc, rhassoul mud powder, mica and mixtures thereof.

16. The sunscreen according to claim 1, wherein the sunscreen comprises anti-caking agent in an amount of from 5 to 20%.

17. The sunscreen according to claim 1, wherein the sunscreen comprises anti-caking agent in an amount of from 5 to 15%.

18. The sunscreen according to claim 1, wherein the anti-caking agent is magnesium carbonate.

19. The sunscreen according to claim 1, further comprising one or more fragrances.

20. The sunscreen according to claim 19, wherein the sunscreen comprises fragrance in an amount of no greater than 5% by weight of the sunscreen.

21. The sunscreen according to claim 1, further comprising a component selected from binders, fillers, fruits, vegetables, humectants, dispersants and mixtures thereof.

22. The sunscreen according to claim 1, further comprising a pigment.

23. The sunscreen according to claim 22, wherein the pigment is a UV reflecting material.

24. The sunscreen according to claim 1, wherein the sunscreen comprises water in an amount of no greater than 5% by weight of the sunscreen.

25. The sunscreen according to claim 1, wherein the sunscreen comprises water in an amount of no greater than 1% by weight of the sunscreen.

26. The sunscreen according to claim 1, wherein the sunscreen comprises preservatives in an amount of no greater than 1% by weight of the sunscreen.

27. A process for the production of a sunscreen in solid form comprising:
   (i) at least one vegetable butter and optionally, vegetable oil, wax, or a mixture of vegetable butter, vegetable oil and/or wax, wherein the vegetable oil, vegetable butter and wax are present in a total amount of from 1 to 25% by weight of the sunscreen,
   (ii) one or more UV absorbing materials, wherein UV absorbing material is present in an amount of from 10 to 40% by weight of the sunscreen,
   (iii) one or more UV reflecting materials, wherein UV reflecting material is present in an amount of from 30 to 85% by weight of the sunscreen, and
   (iv) one or more anti-caking agents, wherein anti-caking agent is present in an amount of from 5 to 25% by weight of the sunscreen, and
   (v) one or more starches,
   the process comprising the steps of
     (a) when the vegetable oil, vegetable butter, wax or mixture thereof is solid, heating the vegetable oil, vegetable butter, wax or mixture thereof to provide a liquid
     (b) mixing the one or more UV absorbing materials, the one or more UV reflecting materials, and the one or more starches with the liquid vegetable oil, vegetable butter, wax or mixture thereof,
     (c) cooling the mixture to provide the solid sunscreen.

28. A method of applying a sunscreen comprising the step(s) of applying to the skin of a user a sunscreen in powder form comprising:
   (i) at least one vegetable butter and optionally, vegetable oil, wax, or a mixture of vegetable butter, vegetable oil and/or wax, wherein the vegetable oil, vegetable butter and wax are present in a total amount of from 1 to 25% by weight of the sunscreen,
   (ii) one or more UV absorbing materials, wherein UV absorbing material is present in an amount of from 10 to 40% by weight of the sunscreen,
   (iii) one or more UV reflecting materials, wherein UV reflecting material is present in an amount of from 30 to 85% by weight of the sunscreen,
   (iv) one or more anti-caking agents, wherein anti-caking agent is present in an amount of from 5 to 25% by weight of the sunscreen, and
   (v) one or more starches.

29. The method according to claim 28, wherein the sunscreen is applied as an additive or as a supplement to other cosmetic products.

30. The sunscreen according to claim 1, wherein the one or more starches are selected from corn starch, potato flour, and mixtures thereof.

31. The sunscreen according to claim 1, wherein the vegetable butter is selected from the group consisting of: cocoa butter, murumuru butter, cupuacu butter, illipe butter, mango butter and mixtures thereof.

* * * * *